United States Patent
Hwang et al.

(10) Patent No.: US 7,851,740 B2
(45) Date of Patent: Dec. 14, 2010

(54) PORTABLE BODY FAT MEASUREMENT DEVICE, METHOD, AND MEDIUM, USING SIDE-VIEW LIGHT SOURCES

(75) Inventors: In Duk Hwang, Yongin-si (KR); Kun Soo Shin, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 11/797,198

(22) Filed: May 1, 2007

(65) Prior Publication Data

US 2007/0293767 A1    Dec. 20, 2007

(30) Foreign Application Priority Data

May 19, 2006    (KR) ............ 10-2006-0044953

(51) Int. Cl.
G06M 7/00    (2006.01)
A61B 6/00    (2006.01)

(52) U.S. Cl. ........................... 250/221; 600/476
(58) Field of Classification Search .......... 250/227.11, 250/227.14–227.24, 221, 559.4; 600/473, 600/476, 310; 356/40–42, 300, 600, 432–442
See application file for complete search history.

(56) References Cited

U.S. PATENT DOCUMENTS

| | | | | |
|---|---|---|---|---|
| 5,014,713 | A | * | 5/1991 | Roper et al. ............. 600/473 |
| 5,057,695 | A | * | 10/1991 | Hirao et al. ............. 250/575 |
| 5,299,570 | A | * | 4/1994 | Hatschek ............. 600/479 |
| 5,490,506 | A | * | 2/1996 | Takatani et al. ............. 600/309 |
| 5,598,842 | A | * | 2/1997 | Ishihara et al. ............. 600/322 |
| 5,830,132 | A | * | 11/1998 | Robinson ............. 600/310 |
| 6,078,833 | A | | 6/2000 | Hueber |
| 6,285,904 | B1 | | 9/2001 | Weber et al. |
| 6,315,955 | B1 | * | 11/2001 | Klein ............. 422/73 |
| 6,584,340 | B1 | * | 6/2003 | Horiuchi et al. ............. 600/473 |

(Continued)

FOREIGN PATENT DOCUMENTS

EP    0819970 A1    1/1998

(Continued)

OTHER PUBLICATIONS

Korean Office Action for corresponding Korean Patent Application No. 10-2006-0044953 dated Jul. 27, 2007.

(Continued)

*Primary Examiner*—Que T Le
*Assistant Examiner*—Jennifer Bennett
(74) *Attorney, Agent, or Firm*—Staas & Halsey LLP (57) ABSTRACT

A portable body fat measurement device, method and medium that can accurately measure body fat by using a small optical sensor having a comparatively small cross-section. The device includes a light source unit having at least two side-view light sources and a light guiding efficiency optical element to guide an optical signal generated from the at least two side-view light sources to a measuring point, an optical detection unit to detect a scattered optical signal, generated by a scattering of the optical signal irradiated to the measuring point, and to transform the scattered optical signal into an electrical signal; and an electrical signal calculation unit to calculate body fat information based on the electrical signal.

27 Claims, 3 Drawing Sheets

U.S. PATENT DOCUMENTS

| | | |
|---|---|---|
| 7,251,513 B2 * | 7/2007 | Kondoh et al. ............... 600/310 |
| 2002/0183624 A1 | 12/2002 | Rowe et al. |
| 2004/0111035 A1 | 6/2004 | Kondoh et al. |

FOREIGN PATENT DOCUMENTS

| | | |
|---|---|---|
| EP | 1396227 A1 | 3/2004 |
| EP | 1520514 A1 | 4/2005 |
| EP | 1634533 A1 | 3/2006 |
| JP | 2000-155091 | 6/2000 |
| JP | 2000-237195 | 9/2000 |
| JP | 2002-27051 | 1/2002 |
| JP | 2003-265440 | 9/2003 |
| JP | 2004-350836 | 12/2004 |
| KR | 2001-0008540 | 2/2001 |
| KR | 2001-0099267 | 11/2001 |
| KR | 2001-0106960 | 12/2001 |
| KR | 2002-0088833 | 11/2002 |
| KR | 10-2004-0101043 | 12/2004 |
| KR | 10-2004-0106833 | 12/2004 |
| KR | 10-2005-0103355 | 10/2005 |
| KR | 10-2005-0105783 | 11/2005 |
| WO | WO 01/28416 A1 | 4/2001 |

OTHER PUBLICATIONS

European Search Report for corresponding European Patent Application No. 07107810.9 dated Aug. 9, 2007, 6 pages (In English).

European Search Report for corresponding European Patent Application No. 07075331.4 dated Apr. 20, 2010, 7 pgs (in English).

U.S. Appl. No. 11/797,199, filed May 1, 2007, in Duk Hwang, et al.

Office Action dated Aug. 19, 2009 for related U.S. Appl. No. 11/797,199.

Office Action dated Nov. 6, 2009 for related U.S. Appl. No. 11/797,199.

Office Action dated Dec. 23, 2009 for related U.S. Appl. No. 11/797,199.

Office Action dated Mar. 10, 2010 for related U.S. Appl. No. 11/797,199.

* cited by examiner

PORTABLE BODY FAT MEASUREMENT DEVICE, METHOD, AND MEDIUM, USING SIDE-VIEW LIGHT SOURCES

CROSS-REFERENCE TO RELATED APPLICATIONS

This application claims the benefit of Korean Patent Application No. 10-2006-0044953, filed on May 19, 2006, in the Korean Intellectual Property Office, the disclosure of which is incorporated herein by reference.

BACKGROUND

1. Field

One or more embodiments of the present invention relate to a portable body fat measurement device, method, and medium using side-view light sources and an optical sensor module, and more particularly to a portable body fat measurement device, method and medium which can irradiate an output light from the side-view light sources to a measurement point for body fat measurement, and calculate body fat information by using a light scattered at the measurement point.

2. Description of the Related Art

Maintaining health and achieving beauty is a priority for many consumers. Accordingly, there is currently a trend to seek a healthy lifestyle. The amount of body fat is one criteria used to estimate an individual's health. There are various methods of measuring the amount of body fat.

Methods for measuring body fat ratio include a body average density measurement employing underwater weighing, a skinfold test measuring the thickness of fat at a specific point of the body, applying a weak electrical current to the body and measuring the body's impedance, and using a table of values to measure the body fat ratio based on waist size. Problems associated with these methods include inaccuracy and the need for complicated equipment.

Currently, body fat measurement techniques also include using measuring light from a body to readily and accurately measuring body fat. Such body fat measurement device using light operates based on the principal that backward scattering occurs when a light emitted from a light source is used to irradiate a measurement point of a body. An optical detector is used to measure the amount of body fat by measuring a scattered optical signal.

A general issue with such body fat measurement devices, using backscattered light, is that the light source is generally too big to be incorporated into a portable device. Moreover, when the device is miniaturized, accuracy of the body fat measurement device may not be guaranteed because the accuracy of the body fat measurement device depends on an irradiated dimension of the light, and on an optical volume. Accordingly, a portable body fat measurement device that can readily and accurately measure body fat thickness is needed.

SUMMARY

One or more embodiments of the present invention provide a portable body fat measurement device, method and medium, which can more accurately measure body fat by minimizing a measurement error caused by hemoglobin. For example, a signal requesting a change of the measurement point may be output in an image output unit and sound output unit when body fat is measured by irradiating a measurement point of a user to indicate when a blood vessel is located beneath the measurement point.

One or more embodiments of the present invention also provide a portable body fat measurement device, method and medium, that may also be installed within portable devices, e.g., a mobile terminal and the like, by minimizing thickness of an optical sensor module installed in the portable body fat measurement device.

One or more embodiments of the present invention also provides a portable body fat measurement device, method and medium, that can accurately measure body fat by using a small optical sensor having a comparatively small cross-section, by adopting an optical element, e.g., a prism sheet and a diffusion plate.

Additional aspects and/or advantages of the invention will be set forth in part in the description which follows and, in part, will be apparent from the description, or may be learned by practice of the invention.

According to one or more embodiments of the present invention, there is provided a portable body fat measuring device including a light source unit having at least two side-view light sources and a light guiding efficiency optical element to guide an optical signal generated from the at least two side-view light sources to a measuring point at which body fat is measured, an optical detection unit to detect a scattered optical signal, generated by a scattering of the optical signal irradiated to the measuring point, and to transform the scattered optical signal into an electrical signal, and an electrical signal calculation unit to calculate body fat information based on the electrical signal.

According to one or more embodiments of the present invention, there is provided an optical sensor module of a portable body fat measuring device, the optical sensor module including a light source unit having at least two side-view light sources and a light guiding efficiency optical element to guide an optical signal generated from the at least two side-view light sources to a body fat measuring point at which body fat is measured, and an optical detection unit to detect a scattered optical signal, generated by scattering of the optical signal irradiated to the measuring point, to transform the scattered optical signal into an electrical signal, and to forward the electrical signal to an electrical signal calculation unit.

According to one or more embodiments of the present invention, there is provided method for measuring body fat using a portable light source unit having at least two side-view light sources and a light guiding efficiency optical element including guiding at least one light beam generated from the at least two side-view light sources to irradiate a measuring point, detecting scattered light, generated by a scattering of the at least one light beam after being irradiated to the measuring point transforming the scattered light into an electrical signal, and calculating body fat information based on the electrical signal.

BRIEF DESCRIPTION OF THE DRAWINGS

These and/or other aspects and advantages of the present invention will become apparent and more readily appreciated from the following detailed description, taken in conjunction with the accompanying drawings of which.

DETAILED DESCRIPTION OF EMBODIMENTS

Reference will now be made in detail to embodiments of the present invention, examples of which are illustrated in the accompanying drawings, wherein like reference numerals refer to the like elements throughout. Embodiments are described below in order to explain the present invention by referring to the figures.

A body fat measurement apparatus, according to an embodiment of the present invention, may be designed to have a stand-alone configuration, or the apparatus may be installed in a portable device such as a mobile communication device, a personal digital assistant (PDA), a portable game device, an MP3 player, a personal multimedia player (PMP), a digital multimedia broadcasting (DMB) device, a blood sugar measurement device, a grip power exercise device, a notebook computer, etc., for example, noting that alternative embodiments are equally available.

Further, measurement techniques described herein are not limited to a human body. The portable body fat measurement device, according to one or more embodiments of the present invention, may be used for at least all organisms having a subcutaneous fat layer between skin and muscle, for example.

Figure 1:
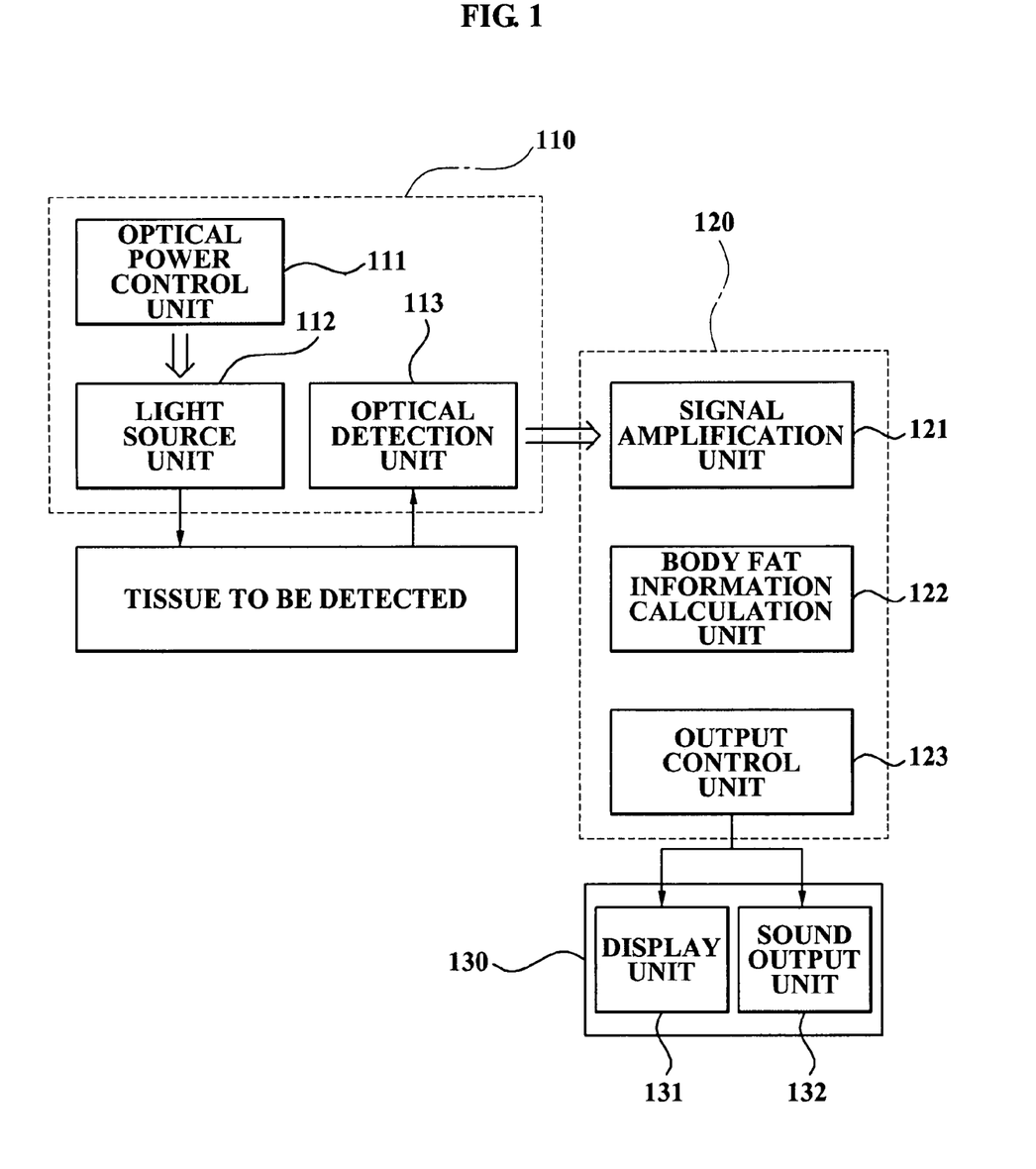
FIG. 1 illustrates a configuration of a portable body fat measurement device, according to one or more embodiments of the present invention.

FIG. 1 illustrates a configuration of a portable body fat measurement device according to one or more embodiments of the present invention.

The portable body fat measurement device may include, for example, an optical sensor module 110, an electrical signal calculation unit 120 and an output unit 130. The optical sensor module 110 may include, also as an example, an optical power control unit 111, a light source unit 112 and an optical detection unit 113. The electrical signal unit 120 may include, similarly as an example, a signal amplification unit 121, a body fat information calculation unit 122 and an output control unit 123, with output unit 130, potentially also includes a display unit 131 and a sound output unit 132.

The light source unit 112 of the optical sensor module 110 may have at least two side-view light sources and a light guiding efficiency optical element guiding an optical signal generated from the side-view light sources to a body fat measurement point.

The light source unit 112 may include, for example, the light guiding efficiency optical element, e.g., a light emitting diode (LED), a light guide plate, and/or an optical fiber. Here, the light guiding efficiency optical element may guide light generated in the side-view light sources to vertically irradiate a body at the measurement point, using a predetermined dimension. The side-view light sources may be embodied using a luminous element, e.g., an LED, located in the light guiding efficiency optical element. for such an embodiment, the configuration and shape of the side-view light sources included in a light source unit 112 will be described in greater detail below with reference to FIG. 3.

Figure 3:
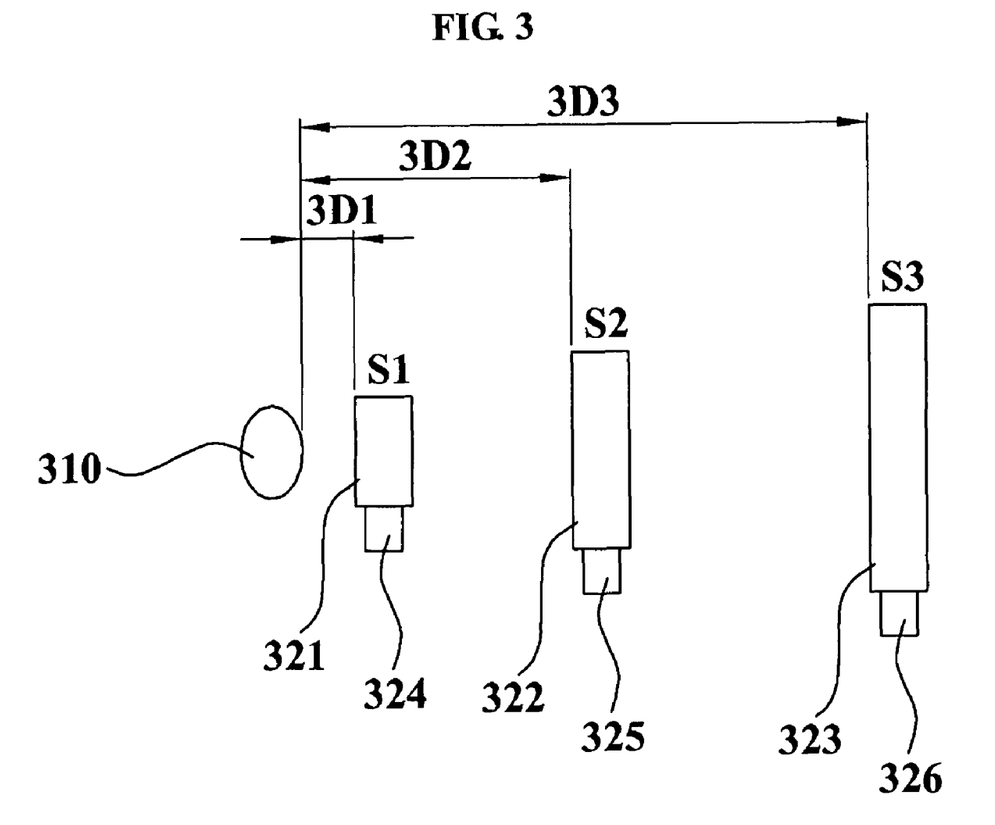
FIG. 3 illustrates a top view of an optical sensor module, according to one or more embodiments of the present invention.

FIG. 3 illustrates a top view of an optical sensor module of a portable body fat measurement device, according to one or more embodiments of the present invention.

Referring to FIGS. 1 and 3, a top view of an optical sensor module includes, for example, a light source unit 112 and a light detection unit 113 of the optical sensor module 110. According to one or more embodiments of the present invention, the optical sensor may include at least two of the light source unit 112, i.e., the optical sensor may include at least two of the light source unit 112 for measuring body fat thickness. In another embodiment, the optical sensor may include at least three of the light source unit 112 for more accurate measurements the body fat thickness. As the quantity of the light source unit 112 increases, a scattered light reference, which may be used to measure the body fat at a measurement point, may increase. This may improve the accuracy of the measurements.

As an example, in FIG. 3, three light source units, i.e., a light source S1, a light source S2, and a light source S3 are installed.

Referring to FIG. 3, the light source units S1, S2, and S3 may include side-view light sources 324, 325 and 326, and light guiding efficiency optical elements 321, 322 and 323. Specifically, as an example, one of the light source units S1, S2, and S3 may be installed along a lateral face of the light guiding efficiency optical elements 321, 322 and 323, noting that additional light source units may further be installed along the lateral face of the light guiding efficiency optical elements 321, 322 and 323.

An installation quantity and position of the side-view light sources 324, 325 and 326 may be embodied using various methods. The side-view light sources 324, 325 and 326 may be embodied with a luminous element, e.g., with the LED example described above.

The light guiding efficiency optical elements 321, 322 and 323 receive light from the side-view light sources 324, 325 and 326 and may guide the emitted light to be emitted via a top surface of the light guiding efficiency optical elements 321, 322 and 323. Specifically, light may be radiated in the same dimension as the top surface of the light guiding efficiency optical elements 321, 322 and 323.

The light guiding efficiency optical elements 321, 322 and 323 may include a prism sheet to increase the forward luminance of light reflected via the prism sheet. Here, light having a predetermined angle may exclusively be transmitted, for example, and all light radiated at all other angles may be reflected to increase forward luminance.

In addition, the light guiding efficiency optical elements 321, 322 and 323 may include a diffusion plate, i.e. the diffusion plate may be provided along the top surface of the light guiding efficiency optical elements 321, 322 and 323, so that uniform luminance according to a viewing angle may be achieved. The diffusion plate may be embodied, for example, in a polyethylene terephthalate (PET), a poly carbonate (PC), or the like. In another embodiment, a particle coating film for scattering light may also be formed on a top surface of the light guiding efficiency optical elements 321, 322 and 323, e.g., provided with the diffusion plate.

As illustrated, the light source units S1, S2 and S3, including the side-view light sources 324, 325 and 326 and the light guiding efficiency optical elements 321, 322 and 323, may be spaced apart from the optical detection unit 310 by a predetermined distance, e.g., the light source unit S1 may be separated from the optical detection unit 310 by a distance 3D1, the light source unit S2 may be separated from the optical detection unit 310 by a distance 3D2, and the light source unit S3 may be separated from the optical detection unit 310 by a distance 3D3. The distances 3D1, 3D2 and 3D3 between each of the light source units S1, S2, and S3, respectively, and the optical detection unit 310, may be variously designed according to a threshold value for measurable body fat at a measurement point. Namely, when the distance is larger, the threshold value of the measurable body fat at the measurement point becomes comparatively larger.

Also, an optical power or light strength output from the side-view light sources 324, 325, and 326 of each of the light source units may be designed to increase as the distances 3D1, 3D2, and 3D3 from the optical detection unit 310 increase. Namely, the optical power may be established to correspond to the respective powers of the side-view light source 326 of the optical source S3, the side-view light source 325 of the optical source S2 and the side-view light source 324 of the optical source S1. The setting of the optical power may be controlled by the optical power control unit 111, for example. In one embodiment, light output from each of the side-view light sources 324, 325, and 326 may be made identical to any of the other light sources.

In another embodiment, the light source units S1, S2, and S3 including the side-view light sources 324, 325, and 326 and the light guide plate may be designed to have a thickness of less than approximately 1.5 mm. This facilitates installation in a portable device, for example. As described above, a slimmer light source unit capable of outputting a sufficient optical power may be provided by establishing at least two side-view light sources in a peripheral of the light guiding efficiency optical elements 321, 322 and 323, e.g., in an array type. Accordingly, depending on the environment, the optical sensor module 110, according to one or more embodiments of the present invention, may be optimized for installation in a mobile terminal where an acceptable component thickness is extremely limited, due to the density of components within the mobile device.

Referring back to FIG. 1, such an optical power control unit 111 may control the light power generated by controlling current supplied to the at least two side-view light sources. As described above, the operational current supplied to the at least two side-view light sources may be controlled so as to increase the optical power in proportion to the distance of a side-view light source from the optical detection unit 113.

The optical detection unit 113 may receive at least two scattered lights at the measurement point to transform into an electrical signal. Namely, the optical detection unit 113 may receive light scattered from inside a body as a result of the measurement point being irradiated. In one embodiment, the optical detection unit 113 may include an optical-electrical transducer element to transform the optical signal into the electrical signal.

The electrical signal calculation unit 120 may calculate body fat data at the measurement point by reviewing the corresponding electrical signal. As an example only, the electrical signal calculation unit 120 may include a signal amplification unit 121, a body fat information calculation unit 122 and an output control unit 123.

The signal amplification unit 121 may receive and amplify the electrical signal, e.g., transformed in the optical detection unit 113, and forward/transmit the signal to the body fat information calculation unit 122.

The body fat information calculation unit 122 may use the amplified electrical signal to calculate body fat information at the measurement point. The body fat information calculation unit 122 may further calculate thickness of the body fat from a intensity of scattered light backscattered from a body. The body fat ratio may also be calculated as a percentage, or a weight of the body fat may be calculated via a predetermined lookup table, which will be described below by referring to FIG. 2.

Figure 2:
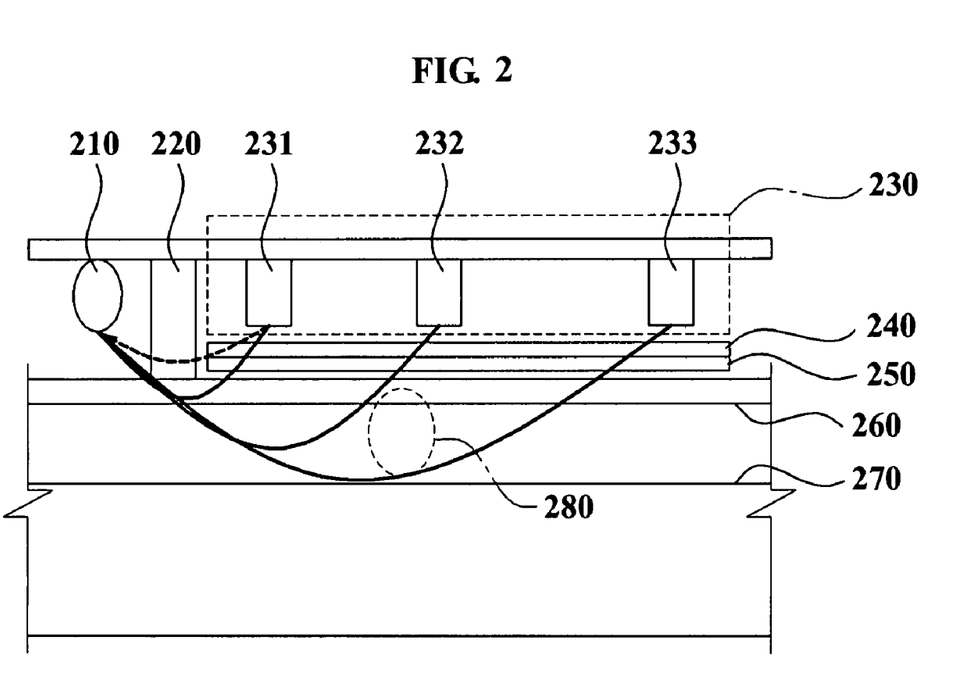
FIG. 2 illustrates a lateral face of an optical sensor module, according to one or more embodiments of the present invention.

FIG. 2 illustrates, as an example only, a lateral face of an optical sensor module of a portable body fat measurement device according to one or more embodiments of the present invention.

As described, the light source unit 230 may include at least one side-view light sources 231, 232 and 233, a prism sheet 240 and a diffusion plate 250. For example, in FIG. 2, a light source unit 230 may have three side-view light sources 231, 232 and 233, a prism sheet 240 and a diffusion plate 250.

Each of the side-view light sources 231, 232 and 233 may be separated from the optical detection unit 210 by a certain distance. The optical power control unit 111 of FIG. 1 may further control a value of the operation current supplied to each of the light sources. Such control compensates for the fact that an irradiated optical power may increase, as a distance from the optical detection unit 210 increases. Namely, as illustrated in FIG. 2, the current supplied to the side-view light source 233 may be greater than a corresponding current supplied to the side-view light source 232, and current supplied to the side-view light source 232 may be greater than corresponding current supplied to the side-view light source 231.

In this case, the intensity of scattered light, radiated from the side-view light source 233, scattered from a body and received by the optical detection unit 210, is smaller than the intensity of scattered light received by the optical detection unit from the side-view light source 232. Similarly, the intensity of scattered light corresponding to the side-view light source 232, is smaller than the intensity of scattered light corresponding to the side-view light source 231. Specifically, intensity of scattered light, reflected in different directions in different layers, e.g., layer 270 between a fat layer and a muscle layer, may be varied. Therefore the body fat information calculation unit 122 may calculate body fat information at the measurement point by calculating the intensity of scattered light corresponding to the each of the light sources.

The optical detection unit 210 detects scattered light, generated from each of the side-view light sources 231, 232 and 233, irradiated and scattered into the body. The illustrated three solid lines in FIG. 2 indicate optical signals that have been generated by each of the side-view light sources 231, 232 and 233 to irradiate a measurement point on a body. The optical signals, generated by each of the side-view light sources 231, 232 and 233, are scattered into the body and subsequently detected by the optical detection unit 210.

Here, an optical cut-off unit 220 is provided to prevent the lights, illustrated as a dotted line in FIG. 2 and generated by each of the side-view light sources 231, 232 and 233, from being directly detected in the optical detection unit 210 without first being irradiated and scattered into the body. Such direct radiation may cause an inaccurate measurement in one or more embodiments of the present invention.

The intensity of the scattered light, generated in the side-view light sources 231, 232 and 233, decreases in proportion to the distance the scattered light travels inside the body. Also, the intensity of the scattered light tends to be reduced significantly as the scattered light passes through the layer 260 between the skin and the fat and the layer 270 between the fat and the muscle. In this case, information about the scattered light may be gained by sequentially extinguishing each of the side-view light sources 231, 232 and 233. Various body fat information, e.g. thickness of body fat, a body fat ratio, weight of the body fat and the like, may be calculated from the information gained by sequentially extinguishing each of the side-view light sources 231, 232 and 233.

Referring back to FIG. 1, an output control unit 123 controls the body fat information to be displayed or played via the output unit 130. For example, the output unit 130 may display or play the body fat information via a display unit 131 or a sound output unit 132. Alternatively, output and/or display embodiments are equally available.

Here, when the electrical signal transformed by the signal amplification unit 121 meets a predetermined value, e.g. is less than or equal to the predetermined value, the output control unit 123 may generate a message, requesting a user to change the measurement point. The message may be displayed and/or played via the output unit 130, for example. Specifically, as only an example, when the body fat information calculation unit 122 is not able to calculate body fat thickness because the electrical signal is weak, the output control unit 123 may provide the user with a message, requesting the user to change the measurement point, via the output unit 130.

Referring to FIG. 2, when a blood vessel 280 is located at or near the measurement point, the electrical signal may be weak. Blood flowing through the blood vessel 280 includes hemoglobin. A property of hemoglobin causes it to absorb scattered light. Due to hemoglobin's absorption of scattered light, when a measurement point is at or near a blood vessel, the intensity of scattered light received by the optical detection unit 210 decreases, possibly resulting in inaccurate body fat measurements.

Accordingly, when a value of the electrical signal meets a predetermined value, e.g. is less than or equal to the predetermined value, the output control unit 123 may provide the user with a message requesting the user to change the measurement point. The message may be displayed in a display unit 131, for example, using a type of a short message service (SMS). The message may also be played via the output unit 132 as audio sound, such as an alarm signal or a voice message, for example.

According to one or more embodiments of the present invention, to improve accuracy when scattered light is absorbed by hemoglobin, at least any one of the at least two side-view light sources may output a light having a wavelength of approximately 600 nm through 800 nm, which provides comparatively greater absorption for hemoglobin.

When at least any one of the side-view light sources radiates light having a wavelength of approximately 600 nm through 800 nm, the optical detection unit 210 may more accurately detect a signal when it is located above a blood vessel. The optical detection unit 210 may then request a user to change the measurement point. Namely, according to one or more embodiments of the present invention, a plurality of light sources may radiate light having a wavelength of approximately 600 nm through 950 nm, and more specifically at least one of the plurality of light sources may irradiate a light having a wavelength of approximately 600 nm through 800 nm, to more accurately detect a signal when the optical detection unit 210 is located above a blood vessel. Here, alternative embodiments are equally available.

Thus, according to one or more embodiments of the present invention, a measurement error when measuring body fat thickness may be minimized by preventing a portable body fat measurement device 100 from being located above a blood vessel.

In addition to this discussion, embodiments of the present invention can also be implemented through computer readable code/instructions in/on a medium, e.g., a computer readable medium, to control at least one processing element to implement any above described embodiment. The medium can correspond to any medium/media permitting the storing and/or transmission of the computer readable code.

The computer readable code can be recorded/transferred on a medium in a variety of ways, with examples of the medium including magnetic storage media (e.g., ROM, floppy disks, hard disks, etc.), optical recording media (e.g., CD-ROMs, or DVDs), and storage/transmission media such as carrier waves, as well as through the Internet, for example. Here, the medium may further be a signal, such as a resultant signal or bit stream, according to embodiments of the present invention. The media may also be a distributed network, so that the computer readable code is stored/transferred and executed in a distributed fashion. Still further, as only an example, the processing element could include a processor or a computer processor, and processing elements may be distributed and/or included in a single device.

Also, according to one or more embodiments of the present invention, a portable body fat measurement device, method and medium, that can more accurately measure body fat by minimizing a measurement error caused by hemoglobin is provided. In an example, a signal for requesting a user to change a measurement point is output to one or both of an image output unit and a sound output unit when a blood vessel is located beneath the measurement point.

Accordingly, according to one or more embodiments of the present invention, a portable body fat measurement device, method and medium, having an optical sensor module of limited thickness is provided, thus facilitating installation in portable devices, e.g. a mobile terminal, with minimal space availability.

Further, according to one or more embodiments of the present invention, a portable body fat measurement device, method and medium, is provided that can accurately measure body fat using an optical sensor with a comparatively smaller cross-section, by adopting an optical element, e.g. a prism sheet and a diffusion plate.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A portable body fat measuring device comprising:
    a light source unit having at least two side-view light sources and a light guiding efficiency optical element to guide an optical signal generated from the at least two side-view light sources to a measuring point at which body fat is measured;
    an optical detection unit to detect a scattered optical signal, generated by a scattering of the optical signal irradiated to the measuring point, and to transform the scattered optical signal into an electrical signal; and
    an electrical signal calculation unit to calculate body fat information based on the electrical signal,
    wherein an optical power output of each of the at least two side-view light sources differs according to a distance of a side-view light source from the optical detection unit.

2. The device of claim 1, wherein the device further comprises an optical power control unit to control a current supplied to the light source unit.

3. The device of claim 1, wherein the at least two side-view light sources emit a light having an identical wavelength, while being separated from the optical detection unit by different distances, such that a power of the optical signal output from the light source unit increases, as a distance between the optical detection unit and the at least two side-view light sources increases.

4. The device of claim 1, wherein the light source unit further comprises a light collective optical element comprising a prism sheet.

5. The device of claim 1, wherein the light source unit further comprises a scattered optical element comprising a diffusion plate.

6. The device of claim 1, wherein the light guiding efficiency optical element comprises a light guide or an optical fiber, and the side-view light source comprises a luminous element including a light emitting diode (LED) located in the light guiding efficiency optical element.

7. The device of claim 1, wherein the electrical signal calculation unit comprises:
a signal amplification unit to amplify the electrical signal transformed from the optical detection unit;
a body fat information calculation unit to calculate the body fat information from the amplified electrical signal; and
an output control unit to control an output of the body fat information to an output device.

8. The device of claim 7, wherein the output control unit controls output of a message to request changing the measuring point via the output device, when intensity of the electrical signal transformed in the optical detection unit meets a predetermined value.

9. The device of claim 1, wherein the light source unit outputs an optical signal having a wavelength of approximately 600 to 800 nm.

10. The device of claim 1, further comprising:
a light cut-off unit to prevent the optical signal from being directly radiated into the optical detection unit.

11. The device of claim 1, wherein the portable body fat measuring device is any one of a mobile terminal, a personal digital Assistant (PDA), a portable game device, an MP3 player, a personal multimedia player (PMP), a digital multimedia broadcasting terminal (DMB) terminal, a portable blood sugar measuring device, and a grip power exercise device.

12. An optical sensor module of a portable body fat measuring device, the optical sensor module comprising:
a light source unit having at least two side-view light sources and a light guiding efficiency optical element to guide an optical signal generated from the at least two side-view light sources to a body fat measuring point at which body fat is measured; and
an optical detection unit to detect a scattered optical signal generated by scattering of the optical signal irradiated to the measuring point to transform the scattered optical signal into an electrical signal, and to forward the electrical signal to an electrical signal calculation unit,
wherein an optical power output of each of the at least two side-view light sources differs according to a distance of a side-view light source from the optical detection unit.

13. The optical sensor module of claim 12, further comprising:
an optical power control unit to control a current supplied to the light source unit.

14. The optical sensor module of claim 12, wherein the at least two side-view light sources emit a light having an identical wavelength, while separated from the optical detection unit with different distances, and a power of the optical signal output from the light source unit increases, as a distance between the optical detection unit and the at least two side-view light sources increases.

15. The optical sensor module of claim 12, wherein the light source unit further comprises a light collective optical element comprising a prism sheet.

16. The optical sensor module of claim 12, wherein the light source unit further comprises a scattered optical element comprising a diffusion plate.

17. The optical sensor module of claim 12, wherein the light guiding efficiency optical element comprises a light guide or an optical fiber, and the side-view light source comprises a luminous element including a light emitting diode (LED) located in the light guiding efficiency optical element.

18. The optical sensor module of claim 12, wherein the electrical signal calculation unit calculates body fat information at the measuring point.

19. A method for measuring body fat using a portable light source unit having at least two side-view light sources, a light guiding efficiency optical element, and an optical detection unit, the method comprising:
guiding at least one light beam generated from the at least two side-view light sources to irradiate a measuring point, the at least two side-view light sources each having an optical power output that differs according to a distance of a side-view light source from the optical detection unit;
detecting scattered light, generated by a scattering of the at least one light beam after being irradiated to the measuring point;
transforming the scattered light into an electrical signal; and
calculating body fat information based on the electrical signal.

20. The method of claim 19, further comprising controlling the at least two side-view light sources by controlling an operation current supplied to the at least two side-view light sources.

21. The method of claim 19 further comprising:
controlling the at least two side-view light sources to respectively emit a light having an identical wavelength;
separating the at least two side-view light sources from an optical detector by different distances; and
increasing a power of the light output from the portable light source unit as a distance between the optical detector and the at least two side-view light sources increases.

22. The method of claim 19 wherein the calculating comprises:
amplifying the electrical signal transformed from the scattered light;
calculating body fat information from the amplified electrical signal; and
controlling the output of the body fat information to an output device.

23. The method of claim 19, further comprising directing a message to request changing the measuring point when a value of the electrical signal transformed in the optical detector meets a predetermined value.

24. The method of claim 19, further comprising preventing the scattered light from being radiated directly into the optical detector.

25. At least one medium comprising computer readable code to control at least one processing element to implement the method of claim 19.

26. A portable body fat measuring device comprising:
a light source unit having at least two side-view light sources;
an optical detection unit to detect a scattered optical signal, generated by a scattering of the optical signal irradiated to a point at which the body fat is measured, and to transform the scattered optical signal into an electrical signal; and
a light cut-off unit to prevent the optical signal from being directly radiated into the optical detection unit without first being irradiated and scattered into a body having subcutaneous fat,
wherein an optical power output of each of the at least two side-view light sources differs according to a distance of a side-view light source from the optical detection unit.

27. A method for measuring body fat using a portable light source unit having at least two side-view light sources each separated a different distance from an optical detector, the method comprising:

guiding light generated from each of the at least two side-view light sources to irradiate a measuring point the at least two side-view light sources each having an optical power output that differs according to a distance of a side-view light source from the optical detector; and sequentially extinguishing the at least two side-view light sources while continuing to detect light generated by a scattering of the at least one light beam after being irradiated to the measuring point.

* * * * *